United States Patent [19]
Mikulich et al.

[11] Patent Number: 4,651,721
[45] Date of Patent: Mar. 24, 1987

[54] PENILE PROSTHESIS SYSTEM

[75] Inventors: Michael A. Mikulich, Shakopee; John H. Burton; Christopher H. Porter, both of Minnetonka, all of Minn.

[73] Assignee: American Medical Systems, Inc., Minnetonka, Minn.

[21] Appl. No.: 722,123

[22] Filed: Apr. 10, 1985

[51] Int. Cl.⁴ ............................................. A61F 2/26
[52] U.S. Cl. ..................................................... 128/79
[58] Field of Search ................................. 128/79, 344

[56] References Cited

U.S. PATENT DOCUMENTS

| | | | |
|---|---|---|---|
| 1,690,995 | 11/1928 | Pratt | 128/344 |
| 4,201,202 | 5/1980 | Finney et al. | 128/79 |
| 4,267,829 | 5/1981 | Burton et al. | 128/79 |
| 4,424,807 | 1/1984 | Evans, Sr. | 128/79 |
| 4,532,920 | 8/1985 | Finney | 128/79 |

Primary Examiner—Gene Mancene
Assistant Examiner—Cary E. Stone
Attorney, Agent, or Firm—Arnold, White & Durkee

[57] ABSTRACT

A penile prosthesis system involves the use of an inflatable penile prosthesis which is expandable under pressurization from a flaccid to an erect state. The prosthesis exhibits a low modulus of elasticity in expansion but ultimately reaches a modulus transition after which it exhibits a high modulus of elasticity and resists further expansion. The prosthesis may also be formed of a material which elastically expands from a flaccid to an erect state and elastically contracts thereafter. In its erect state the prosthesis is taut and the surrounding tissue may be similarly taut and pressurized because of the expansion of the prosthesis in girth. If a weakening occurs in the surrounding tissue, the tendancy to form localized penile bulges is limited because of the inability of the prostheis to expand readily beyond its modulus transition.

11 Claims, 8 Drawing Figures

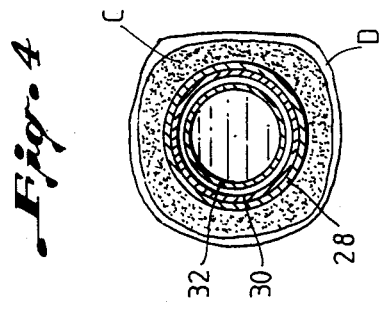
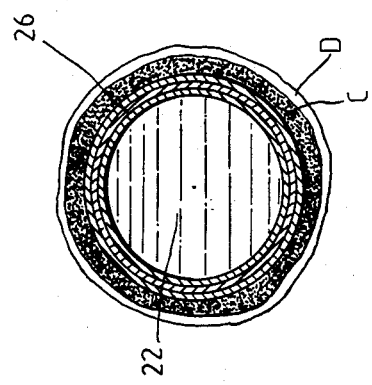
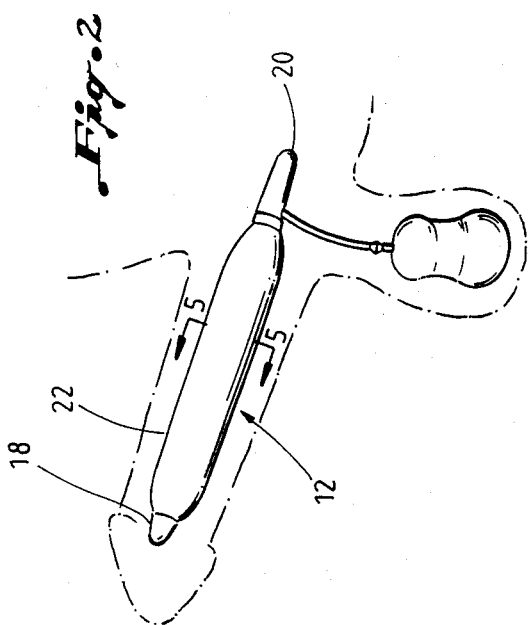
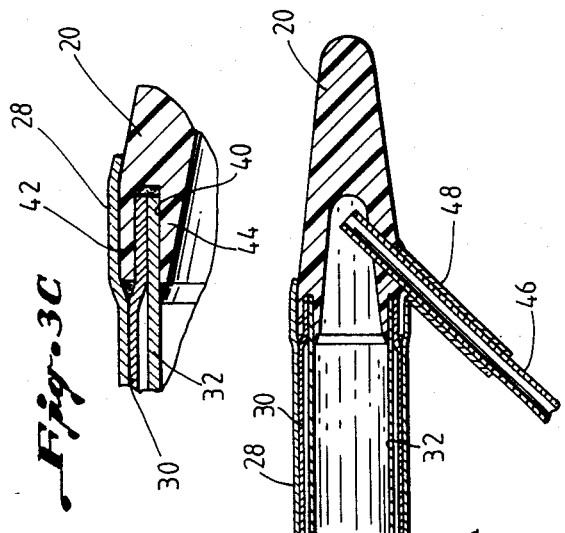
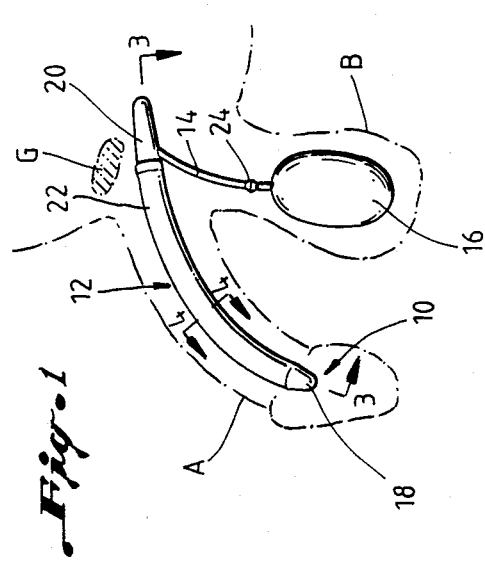
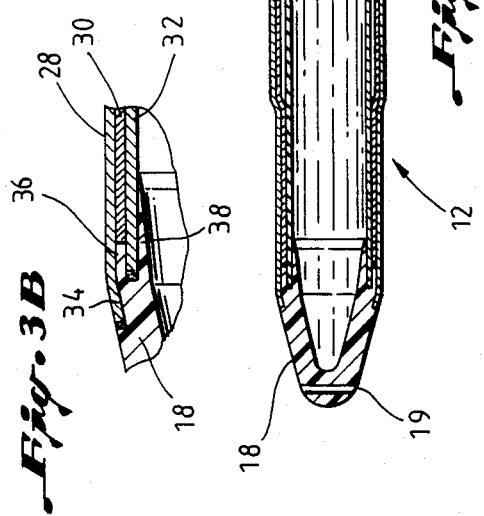

PENILE PROSTHESIS SYSTEM

BACKGROUND OF THE INVENTION

1. Field of the Invention

This invention relates generally to inflatable penile prostheses implantable within one or more corpus cavernosa of the male penis for treating erectile impotency.

2. Brief Description of the Background Art

A wide variety of penile prostheses have been developed in the past which are inflated by pumping a source of fluid into a pressurizable chamber situated in the portion of the penis extending outwardly of the body plane. The pressurization of the inflatable chamber causes the device to be transformed from an angled, bent of flaccid condition to a straight, erect condition. Certain of these devices actually expand upon pressurization in order to stress or tension the user's bodily tissues which surround the implanted device. Specifically, certain devices expand in girth so that the tunic albuginea, which is a fibrous tissue that surrounds the corpus cavernosa, is stressed and placed in tension to simulate the normal biological phenomenon known as erection.

One desirable problem with devices which expand against the tunica albuginea is that weak spots may be present in the tunica which may result in localized bulges (anuerysmal dialation). When the tunica is unable to restrain the artificial prosthesis, the prosthesis may expand through the weak spot in the tunica resulting in a weakened blister or balloon. This blister or balloon may fail resulting in loss of pressurization of the device. While such occurrences are fortunately quite rare, it would be highly desirable to guard against the possibility of bulging brought about by weak spots in the tunica albuginea.

SUMMARY OF THE INVENTION

It is an important feature of the present invention to provide a method and apparatus which helps to limit the formation of localized bulges in the tunica albuginea during pressurization of a penile prosthesis. The present invention also implements such a device which may be efficiently and economically utilized in practice. Moreover, with certain emobidments of the present invention, the apparatus is particularly easily inflated and efficiently deflated following erection.

These and other aspects of the present invention may be achieved by a method of simulating an erection including the step of providing a prosthesis with a pressurizable chamber having a high modulus transition such that the chamber is significantly less expandable after the modulus transition than before the transition. The chamber within the penile prosthesis to is pressurized to cause the prosthesis to undergo relatively low modulus of elasticity expansion in girth until the chamber is tense and erect.

In accordance with another aspect of the present invention a penile prosthesis implantable within one or more corpus cavernosa includes a tubular inflatable housing connectable to a source of pressurizing fluid. The housing defines a pressurizable chamber having a wall with a relatively low modulus of elasticity in expansion. The wall is expandable to a diameter exceeding the relaxed, nonerect diameter of the surrounding tissue, and exhibits a relatively high modulus of elasticity thereafter.

In accordance with yet another aspect of the present invention, a penile prosthesis implantable within one or more corpus cavernosa includes a tubular inflatable housing connectable to a source of pressurizing fluid. The housing defines a pressurizable chamber having walls adapted to expand eleastically in girth to a high modulus transition.

In accordance with another aspect of the present invention, a penile prosthesis implantable within one or more corpus cavernosa includes a tubular inflatable housing connectable to a source of pressurizing fluid. The housing defines a pressurizable chamber having walls adapted to expand elastically in girth to a high modulus transition and to contract elastically in girth when the pressure within the housing decreases.

In accordance with still another aspect of the present invention, a method of simulating a natural penile erection includes the step of pressurizing an expandable chamber within a penile prosthesis to expand the prosthesis in girth and to transform the prosthesis from a flaccid to an erect state. Localized bulging from anueysmal dialation is prevented by limiting the extent of possible relatively low modulus of elasticity expansion of the chamber.

BRIEF DESCRIPTION OF THE DRAWING

FIG. 1 is a side elevational view of one embodiment in use in its flaccid state;

FIG. 2 is a side elevational view of the embodiment shown in FIG. 1 in its erect state;

FIG. 3A is an enlarged cross-sectional view taken generally along the line 3—3 in FIG. 1;

FIG. 3B is an enlarged view of a portion of the left end of the embodiment shown in FIG. 3A;

FIG. 3C is an enlarged view of a portion of the right end of the embodiment shown in FIG. 3A;

FIG. 4 is an enlarged cross-sectional view taken generally along the line 4—4 in FIG. 1;

FIG. 5 is an enlarged cross-sectional view taken generally along the line 5—5 in FIG. 2.

DESCRIPTION OF THE PREFERRED EMBODIMENTS

Figure 6:
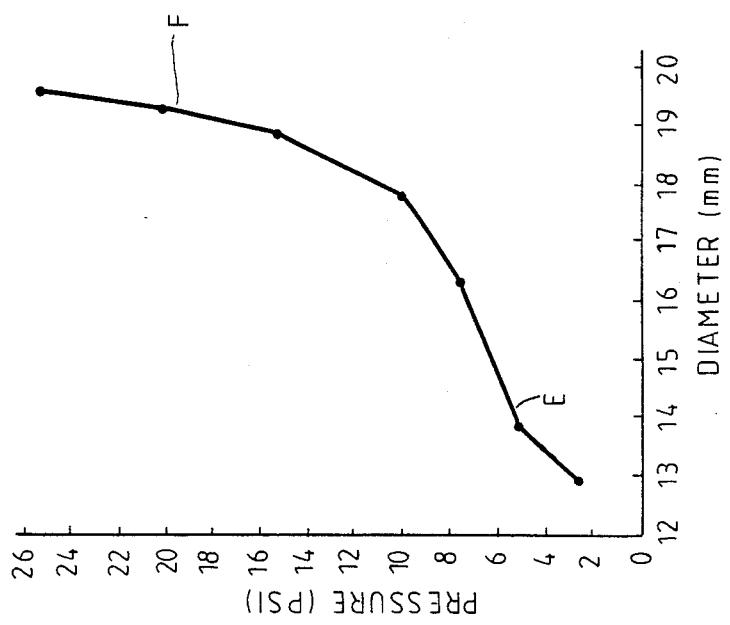
FIG. 6 is a plot of internal applied pressure versus internal diameter for the medial chamber of the embodiment of the present invention shown in FIG. 1.

Referring to the drawing wherein like reference characters are utilized for like parts throughout the several views, an inflatable penile prosthesis 10, shown implanted within a corpus cavernosum of the human penis ("A" in FIG. 1), includes an inflatable generally tubular body 12 sized to fit within a corpus cavernosum in its flaccid state. An inflatable tubular body 12 fluidically connects by tubing 14 to its manually actuatable fluid pump 16, illustrated in position within the scrotal sac "B".

The tubular body 12 includes a front tip 18, a rear tip 20 and medial chamber 22. Advantageously the front tip 18 is relatively rigid so as to resist buckling during intercourse. The front tip 18 may be rigid in both the erect and flaccid states. Thus, as shown in FIG. 3A, the front tip 18 may be formed of relatively thickened flexible material such as silicone rubber. The front tip may include a suture hole 19. Similarly, the rear tip 20 is relatively rigid with respect to the rest of the device. The rear tip 20 may be formed of relatively thickened flexible material such as silicone rubber. Conventionally all external surfaces of the body 12 are formed of a material which is biocompatible, such as silicone.

While the present invention is illustrated with a pump 16 which is external of the body 12, in certain embodiments it may be desirable to provide a pump 16 which is contained within the body 12. In addition while the present invention is described with respect to a pump 16 which is situated in the scrotal sac, it should be understood by those skilled in the art that other external pumps may be utilized including pumps which may be positioned subcutaneously.

The fluid pump 16 is advantageously formed of a flexible, elastic material which may be manually compressed. Fluid, such as a sterile normal saline solution, from a reservoir defined within the pump 16, is then forced into a chamber defined within the tubular body 12. A suitable valve means 24 is provided which allows fluid flow between the pump 16 and body 12 in the direction desired by the patient. One suitable valve for the present purposes is the pull valve shown in U.S. Pat. No. 4,224,934 to Burton and Scott hereby expressly incorporated by reference herein. Conventionally, a single pump 16 is utilized to operate a pair of separate tubular bodies 12 located in different corpus cavernosa. However the present invention is also amenable to use with single unit devices which provide a single body 12 which fills both corpus cavernosa.

Referring to FIGS. 3A and 4, the medial chamber 22 is defined by a tubular housing 26 including a plurality of layers. The tubular housing 26 exhibits a low modulus of elasticity in expansion up to a high modulus transition whereafter the housing 26 exhibits a very high modulus of elasticity such that further expansion, for practical purposes, is prohibited or at least substantially more difficult. After the device passes the high modulus transition, only limited further expansion in girth may be possible in response to relatively higher generated internal pressure.

The expansile behavior of a medial chamber 22 may be characterized by the amount of diameter increase in response to an inrease in internal fluidic pressure. As shown in FIG. 6 for one exemplary embodiment of the present invention, the chamber 22 exhibits a region of relatively lower slope "E" followed by a region of significantly higher slope "F". While the expansile behavior of the chamber 22 may be characterized by its modulus of elasticity under different circumstances, other factors such as chamber shape effects, may also affect the amount of the diameter increase in response to an increase in internal pressure. The phrase "high modulus transition", relating to the pressure versus diameter characteristic of a chamber 22, refers broadly to the transition to a region of significantly higher slope from a region of significantly lower slope.

It should be understood that the high modulus transition may be a single point or it may be a region of intermittently or continuously changing slope. Preferably, the slope of the applied internal pressure versus diameter curve is more than 300% higher after the high modulus transition has been reached. Most preferably, the slope is about 1000% higher after the high modulus transition.

The tubular housing 26 makes the medial chamber 22 at least bistable because it has a first relatively low modulus state of expansion and a second relatively tensioned, nonexpansile or nondistensible state. A variety of materials may be utilized to accomplish this bistability. For example, the housing 26 may be made of a folded or corrugated non-distensible material that essentially unfolds in the first expansile state until it completely unfolds and reaches a modulus transition. A suitable material for such a device is woven polyester fiber such as the one marketed by Dupont under the trade name Dacron. Alternatively, a woven nondistensible fabric which is wrinkled during fabrication to achieve an initial low volume diameter may be utilized as well as a woven nondistensible fabric with longitudinal pleats.

Advantageously however, the tubular housing 26 is made of a material which stretches as it expands to a modulus transition. A device which stretches to a modulus transition eliminates the need for unfolding. These folds may become kinked or blocked resulting in ineffective operation and causing irritation of tissue during expansion.

Suitable materials for implementing a device that stretches to a modulus transition include stretchable polymeric fabrics known as "knits". Patricularly, a knit fabric constructed with a balance between the radial and longitudinal extensibility may be provided such that radial expansion is limited while longitudinal expansion is allowed. Additionally, a woven fabric of multiple threads, some being nondistensible and some being distensible can be utilized. A polymer may also be utilized which has a relationship between stress and strain such that the modulus is low until the specified ultimate diameter is reached and thereafter the modulus is high. At the point of modulus transition, the stress of the polymer is significantly below the stress at which permanent deformation results. Also, woven fabrics having texturized or kinked yarns or fibers may be utilized.

Most advantageously, the present invention is implemented by a tubular housing 26 which elastically expands in a low modulus state to a high modulus transition. After reaching the high modulus transition, the housing possesses a very high modulus of elasticity. The housing advantageously elastically contracts from its expanded state to a nonexpanded state.

A variety of materials may be utilized to implement an embodiment, with a high modulus transition, that elastically expand and contracts. One such material, commonly known as spandex is woven fabric which utilizes a highly elastic polyurethane elastomer core wrapped by a coil of relatively nondistensible polyester fiber which prevents elongation of the composite beyond a pre-set level of distension to provide the modulus transition. The level of distension to provide the modulus transition. The pressure versus diameter characteristic of an exemplary embodiment using such a spandex fabric to form the housing 26 is shown in FIG. 6.

It may be desirable in many circumstances to provide a material with anistropic properties such that the ultimate elongation in a radial or girth direction is less than the ultimate elongation in the longitudinal direction. This may be accomplished using a material that has a modulus in the radial direction which is higher than the modulus in the longitudinal direction. For example, expanded polytetrafluoroethylene (EPTFE), that allows low modulus but limited radial expansion, may be used for this purpose.

For the illustrated medial chamber 22, three different layers of material are utilized. The outer layer 28 may be tubular and may be formed of any material which is biocompatible and elastic and which prevents tissue ingrowth. A suitable material for the outer layer 28 is silicone elastomer. The middle layer 30 may be formed of a material which provides a modulus transition after a period of low modulus expansion. Suitable materials for the middle layer include the bistable materials described above. The inner layer 32 advantageously provides a fluid barrier to define a fluid containing region within the chamber 22. The layer 32 like the layer 28 is advantageously elastic so that it expands to an erect state and immediately resumes its original position upon the cessation of fluid pressurization. If desired a suitable lubricant may be placed between the layers to insure their smooth relative sliding motion with respect to one another.

As illustrated in FIGS. 3A through 3C, the layers 28 to 32 are attached to the front tip 18 and the reat tip 20. Intermediately between the tips 18 and 20 the layers may be unconnected to one another. Conveniently a portion of the medial chamber 22 extends inwardly of the front tip 18 and the rear tip 20 so as to pressurize at least a portion of the interior of the prosthesis 10 during erection. As shown in FIG. 3B, the outer layer 28 may be glued to the front tip 18 on a step 34 defined to receive the left end of the outer layer 28. An annular flange 36 extends outwardly from the front tip 18 to meet and adhesively secure the middle layer 30 while sandwiching the inner layer 32 between itself and a tapered flange 38. The sandwiching of the inner layer 32 between the flanges 36 and 38 enables a fluid tight seal to be achieved. The middle layer 30 may be adhesively secured near its end to the end of the inner layer 32 if necessary.

The tubular housing 26 is secured to the rear tip 20 in essentially the same configuration. However, the middle layer 30 and inner layer 32 are sandwiched together and secured within a slot 40 defined between a pair of overhanging flanges 42 and 44. The outer layer 28 is adhesively secured over the top of the upper overhanging flange 42. This manner of attachment provides a very good seal. The tubing 14 may be adhesively secured to a relatively rigid section of tubing 46 which extends inwardly into the medial chamber 22. A sleeve 48 may surround the rigid tubing 46 to provide further wear protection.

The prosthesis 10 is implanted using now well known surgical procedures. The rear tip 20 may be positioned in the rear of the corpus cavernosum under the puboischiatic rami "G", in FIG. 1.

In operation, the fluid pump 16 is manually compressed to force fluid through the valve 24 into the medial chamber 22. When the pump 16 is released fluid cannot flow back into the pump 16 because of the operation of the valve 24. Thus the user continues to compress the pump 16 to expand the tubular housing 26.

During the initial mode of expansion, the tubular housing 26 has a low modulus of elasticity and thus it expands relatively easily in response to increasing pressurization. As shown in FIG. 4, in its flaccid state, the housing 26 fills the corpus cavernosum "C" but does not stretch the surrounding tissue to any significent degree. As the housing 26 expands in response to increased internal fluid pressure, the surrounding tissue, particularly the tunica albuginea, indicated as "D" in FIGS. 4 and 5, begins to be expanded and placed in tension.

The housing 26 may continue to expand until it reaches a relatively high modulus transition after which continued expansion is particularly difficult. In operation it may not be necessary to pressurize the interior of the housing 26 sufficiently to reach this modulus transition. However, it is normally advantageous that the diameter of the prosthesis, in its erect state, is more than 90% of the diameter when the modulus transition is reached.

It is desirable that the tubular housing 26 be pressurized sufficiently that it becomes tense and erect. Specifically, the device may be transformed from the configuration, shown in FIG. 1, where it bends along the medial chamber 22, to the straight, pressurized configuration, shown in FIG. 2, by sufficiently pressurizing the medial chamber 22. In the pressurized configuration, shown in FIG. 5, the tubular housing 26 is relatively tense and the surrounding tissue including the tunica albuginea is stretched and relatively tense. Therefore a very natural erection is produced.

If a localized weakened area forms in the tunica albuginea, the prosthesis 10 is not prone to form localized bulges because the middle layer 30 expands only to the point when a modulus transition is reached. Once the modulus transition is reached no further expansion is normally possible and thus a localized balloon or blister does not form. The modulus transition is advantageously reached when the prosthesis has an outside diameter within the range of from about 14 to 20 millimeters.

In order to enable the penile prosthesis 10 to be adapted to a variety of different sizes of male organ, the initial diameter of the tubular body 12 is such that the smallest girth penis can be implanted with an adequately sized device. The normal distended diameter of the device, as shown in FIG. 2, usually should then at least equal the largest diameter of the distended male corporal body. Conventional rear tip extenders may be provided to further lessen the need for different prosthesis sizes.

Deflation of the prosthesis may be achieved by opening the valve 24 and allowing fluid to drain back into the pump 16. For example, with the valve shown in the patent incorporated herein by reference, the valve may be opened by manually squeezing the valve.

The present invention enables an inflatable prosthesis to be provided which increases in girth upon erection and therefore may inrease the girth of the surrounding tissues of the penis itself. However the possibility of localized bulging is prevented through the use of a material which reaches a high modulus transition early enough to prevent significant tissue expansion.

While the present invention has been described with respect to a device that uses a multi-layer medial chamber 22, those skilled in the art will appreciate that certain advantages may be achieved with a single layer tubular housing 26 which incorporates all the above-described features.

While the present invention has been described with respect to a limited number of preferred embodiments, those skilled in the art will appreciate a number of variatons and it is intended within the appended claims to cover all such modifications and variations as fall within the true spirit and scope of the present invention.

What is claimed is:

1. A penile prosthesis implantable within one or more corpus cavernosa of the penis to simulate a natural erection and adapted to control aneurysmal dialation, said prosthesis comprising:

a tubular, inflatable chamber communicable with a source of pressurizing fluid to enable the penis to be transformed from a flexible, flaccid state to a relatively stiff, erect state, a body defining said chamber, said body adapted for relatively low modulus of elasticity expansion, in response to pressurization of said chamber, to a diameter exceeding the flaccid diameter of the surrounding tunica albuginea to tension the tunica albuginea, said body creating a relatively high modulus of elasticity against expansion in girth of said body at a diameter greater than the flaccid diameter of the surrounding tunica albuginea but sufficiently small to control aneurysmal dialation.

2. The prosthesis of claim 1 wherein said transition is reached at a diameter of from about 14 to about 20 millimeters.

3. The prosthesis of claim 2 wherein said body elastically expands and contracts.

4. The prosthesis of claim 3 wherein said body is adapted to stretch circumferentially.

5. The prosthesis of claim 4 wherein said body is formed of a plurality of layers including an outer layer which is compatible with human tissue and an inner layer which provides a fluid barrier.

6. A method of simulating a natural erection while controlling aneurysmal dialation with a penile prosthesis adapted to be implanted within the tunica albuginea, comprising the steps of:

providing a tubular inflatable body communicable with a source of pressurizing fluid, said body being expandable to a diameter exceeding the flaccid diameter of the surrounding tunica albuginea to tension the tunica albuginea;

pressurizing said body to cause the body to undergo relatively low modulus of elasticity expansion in girth until the tunica albuginea is tense; and controlling the expansion in girth of said body by providing a high modulus of elasticity transition at a diameter greater than the flaccid diameter of the surrounding tunica albuginea but sufficiently small to control aneurysmal dialation.

7. The method of claim 6 including the step of providing a body that exhibits a ratio of internal pressure to corresponding internal diameter of at least 300% greater after said modulus transition than before said modulus transition.

8. The method of claim 7 wherein said providing step includes the step of providing a body that exhibits a ratio of internal pressure to corresponding internal diameter of about 1,000% greater after said modulus transition than before said modulus transition.

9. The method of claim 8 wherein said modulus transition is provided at a body outside diameter of from about 14 to about 20 millimeters.

10. The method of claim 9 wherein said body is elastically expanded to said modulus transition.

11. The method of claim 10 including the step of pressurizing said prosthesis so that the penis is in an erect state and the diameter of said body is more than 90% of the diameter at the modulus transition.

* * * * *